(12) United States Patent
Zhu et al.

(10) Patent No.: US 7,376,464 B2
(45) Date of Patent: *May 20, 2008

(54) METHOD AND SYSTEM FOR AUTOMATIC ANTI-TACHYCARDIA PACING

(75) Inventors: Qingsheng Zhu, Little Canada, MN (US); Stephen John Hahn, Shoreview, MN (US); Steven D. Girouard, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 604 days.

This patent is subject to a terminal disclaimer.

(21) Appl. No.: 10/914,495

(22) Filed: Aug. 9, 2004

(65) Prior Publication Data

US 2005/0070967 A1 Mar. 31, 2005

Related U.S. Application Data

(63) Continuation of application No. 10/037,302, filed on Oct. 25, 2001, now Pat. No. 6,775,572.

(51) Int. Cl.
*A61N 1/00* (2006.01)
(52) U.S. Cl. ..................................... 607/27
(58) Field of Classification Search ............... 607/4–28
See application file for complete search history.

(56) References Cited

U.S. PATENT DOCUMENTS

| | | | |
|---|---|---|---|
| 4,830,006 A * | 5/1989 | Haluska et al. ................ 607/4 |
| 5,161,529 A * | 11/1992 | Stotts et al. ................... 607/27 |
| 5,209,229 A | 5/1993 | Gilli | |
| 5,222,493 A | 6/1993 | Sholder | |
| 5,224,475 A | 7/1993 | Berg et al. | |
| 5,251,624 A | 10/1993 | Bocek et al. | |
| 5,324,310 A | 6/1994 | Greeninger et al. | |
| 5,330,505 A | 7/1994 | Cohen | |
| 5,342,402 A | 8/1994 | Olson et al. | |
| 5,350,410 A | 9/1994 | Kleks et al. | |
| 5,472,453 A | 12/1995 | Alt | |
| 5,548,619 A | 8/1996 | Horiike et al. | |
| 5,587,970 A | 12/1996 | Greenwood | |

(Continued)

FOREIGN PATENT DOCUMENTS

WO WO-98/40122 9/1998

OTHER PUBLICATIONS

"U.S. Appl. No. 10/835,078, Response filed Aug. 15, 2007 to Final Office Action mailed Jun. 15, 2007", 8 pages.

(Continued)

*Primary Examiner*—Scott M. Getzow
(74) *Attorney, Agent, or Firm*—Schwegman, Lundberg & Woessner, P.A.

(57) ABSTRACT

A method and system for delivering anti-tachycardia pacing is disclosed. A cardiac rhythm management device, such as an implantable pacemaker having anti-tachycardia pacing capability, delivers anti-tachycardia pacing therapy in accordance with an anti-tachycardia pacing protocol upon detection of a terminable arrhythmia. The anti-tachycardia pacing is delivered as a burst of one or more pacing pulses at a specified coupling interval after a sensed ventricular polarization. By sensing if an evoked potential occurs, the device can determine whether or not the anti-tachycardia pacing burst has captured the ventricle and can adjust the coupling interval and/or other parameters accordingly.

20 Claims, 3 Drawing Sheets

U.S. PATENT DOCUMENTS

| | | |
|---|---|---|
| 5,662,688 A | 9/1997 | Haefner et al. |
| 5,683,424 A | 11/1997 | Brown et al. |
| 5,683,431 A | 11/1997 | Wang |
| 5,836,971 A | 11/1998 | Starkweather |
| 5,846,263 A | 12/1998 | Peterson et al. |
| 5,855,593 A | 1/1999 | Olson et al. |
| 5,871,512 A | 2/1999 | Hemming et al. |
| 5,999,854 A | 12/1999 | Deno et al. |
| 6,101,414 A | 8/2000 | Kroll |
| 6,128,529 A | 10/2000 | Elser |
| 6,137,308 A | 10/2000 | Nayak |
| 6,167,308 A | 12/2000 | DeGroot |
| 6,192,275 B1 | 2/2001 | Zhu et al. |
| 6,400,986 B1 | 6/2002 | Sun et al. |
| 6,477,422 B1 | 11/2002 | Splett |
| 6,584,352 B2 | 6/2003 | Combs et al. |
| 6,775,572 B2 | 8/2004 | Zhu et al. |
| 6,885,890 B2 | 4/2005 | Spinelli et al. |
| 2002/0058968 A1 | 5/2002 | Sun et al. |
| 2003/0083703 A1 | 5/2003 | Zhu et al. |
| 2003/0120315 A1 | 6/2003 | Spinelli et al. |
| 2005/0090869 A1 | 4/2005 | Sun et al. |
| 2006/0149325 A1 | 7/2006 | Zhang |

OTHER PUBLICATIONS

Sun, Weimin , et al., "Adaptive Anti-Tachycardia Therapy Apparatus and Method", U.S. Appl. No. 11/267,071, filed Nov. 3, 2005.

* cited by examiner

METHOD AND SYSTEM FOR AUTOMATIC ANTI-TACHYCARDIA PACING

CROSS-REFERENCE TO RELATED APPLICATION

This application is a continuation of U.S. patent application Ser. No. 10/037,302, filed on Oct. 25, 2001, now issued as U.S. Pat. No. 6,775,572, the specification of which is incorporated herein by reference.

FIELD OF THE INVENTION

This invention pertains to methods and system for treating cardiac arrhythmias with anti-tachycardia pacing.

BACKGROUND

Tachyarrhythmias are abnormal heart rhythms characterized by a rapid heart rate, typically expressed in units of beats per minute (bpm). Examples of tachyarrhythmias include supraventricular tachycardias (SVT's) such as sinus tachycardia, atrial tachycardia, and atrial fibrillation. The most dangerous tachyarrythmias, however, are ventricular tachycardia (VT) and ventricular fibrillation (VF). Ventricular rhythms occur when re-entry of a depolarizing wavefront in areas of the ventricular myocardium with different conduction characteristics becomes self-sustaining or when an excitatory focus in the ventricle usurps control of the heart rate from the sinoatrial node. The result is rapid and irregular contraction of the ventricles out of electromechanical synchrony with the atria. Most ventricular rhythms exhibit an abnormal QRS complex in an electrocardiogram because they do not use the normal ventricular conduction system, the depolarization spreading instead from the excitatory focus or point of re-entry directly into the myocardium. Ventricular tachycardia is typically characterized by distorted QRS complexes that occur at a rapid rate, while ventricular fibrillation is diagnosed when the ventricle depolarizes in a chaotic fashion with QRS complexes of constantly changing shape. Both ventricular tachycardia and ventricular fibrillation are hemodynamically compromising, and both can be life-threatening. Ventricular fibrillation, however, causes circulatory arrest within seconds and is the most common cause of sudden cardiac death.

Cardioversion (an electrical shock delivered to the heart synchronously with the QRS complex) and defibrillation (an electrical shock delivered without synchronization to the QRS complex to terminate ventricular fibrillation) can be used to terminate most tachyarrhythmias, including SVT's, VT, and VF. The electric shock terminates the tachyarrhythmia by depolarizing all of the myocardium simultaneously and rendering it refractory. A class of cardiac rhythm management devices known as an implantable cardioverter/defibrillator (ICD) provides this kind of therapy by delivering a shock pulse to the heart when the device detects fibrillation.

Another type of electrical therapy for tachycardia is antitachycardia pacing (ATP). In ATP, the heart is competitively paced with one or more pacing pulses in an effort to interrupt the reentrant circuit causing the tachycardia. Modern ICD's typically have ATP capability so that ATP therapy is delivered to the heart when a tachycardia is detected, while a shock pulse is delivered when fibrillation occurs. Although cardioversion/defibrillation will terminate tachycardia, it consumes a large amount of stored power from the battery and results in patient discomfort owing to the high voltage of the shock pulses. It is desirable, therefore, for the ICD to use ATP to terminate a tachyarrhythmia whenever possible. It is commonly believed that only cardioversion/defibrillation will terminate fibrillation and certain high rate tachycardias, while ATP can be used to treat lower rate tachycardias. A tachyarrhythmia that is regarded as terminable by ATP therapy, based upon rate or other factors, will be referred to herein as either a terminable tachyarrhythmia or a tachycardia.

In most ICD's with ATP capability, ventricular fibrillation (VF) is distinguished from ventricular tachycardia (VT) using rate-based criteria so that ATP or shock therapy can be delivered as appropriate. The heart rate is usually measured by detection of the time between successive R waves (i.e., ventricular depolarizations). A measured heart rate is classified as a tachycardia when the rate is in a VT zone, defined as a range of rates above a tachycardia detection rate (TDR) but below a fibrillation detection rate (FDR). A measured heart rate above the FDR, on the other hand, is in the VF zone and is classified as fibrillation. In a typical device, a tachyarrhythmia with a heart rate in the VT zone is treated with ATP therapy in order to avoid an unnecessary painful shock to the patient, and a defibrillation shock is delivered if the pacing fails to terminate the tachyarrhythmia. It is a primary objective of the present invention to provide a method and apparatus for delivering ATP therapy in a manner that increases the likelihood that ATP therapy will terminate a tachyarrhythmia without resorting to a defibrillation shock. The approach described below uses capture verification to determine whether a pacing pulse delivered in accordance with a particular ATP protocol captures the myocardium so that appropriate adjustments to the protocol can be made.

SUMMARY OF THE INVENTION

ATP therapy is only effective when the ATP pacing pulses actually capture the myocardium. Present ATP protocols, however, are open loop systems that do not use any type of feedback to the device to confirm that capture has occurred. The present invention is a method and device for the delivery of anti-tachycardia pacing (ATP) therapy upon detection of a tachyarrhythmia with verification of capture by the pacing pulses. To deliver ventricular ATP therapy, a burst of one or more pacing pulses is delivered in accordance with a particular ATP protocol, where the burst is output after a specified coupling interval with respect to a ventricular sense. By sensing whether an evoked response occurs during a capture detection window following the output of a pacing pulse, it is determined whether the pulse has captured the ventricle. Such capture verification can then be used to adaptively adjust the value of the coupling interval, cycle length, or other ATP parameters, thus improving the outcome of ATP protocols.

DETAILED DESCRIPTION

In the description that follows, a microprocessor-based cardiac rhythm management device will be referred to as incorporating the system and method that is the present invention. In the embodiment to be described, the invention is implemented with a control unit made up of a microprocessor executing programmed instructions in memory. It should be appreciated, however, that certain functions of a cardiac rhythm management device could be controlled by custom logic circuitry either in addition to or instead of a programmed microprocessor. The term "controller" as used herein should therefore be taken to encompass either custom circuitry (i.e., dedicated hardware) or a microprocessor executing programmed instructions contained in a processor-readable storage medium along with associated circuit elements.

1. Hardware Platform

Figure 1:
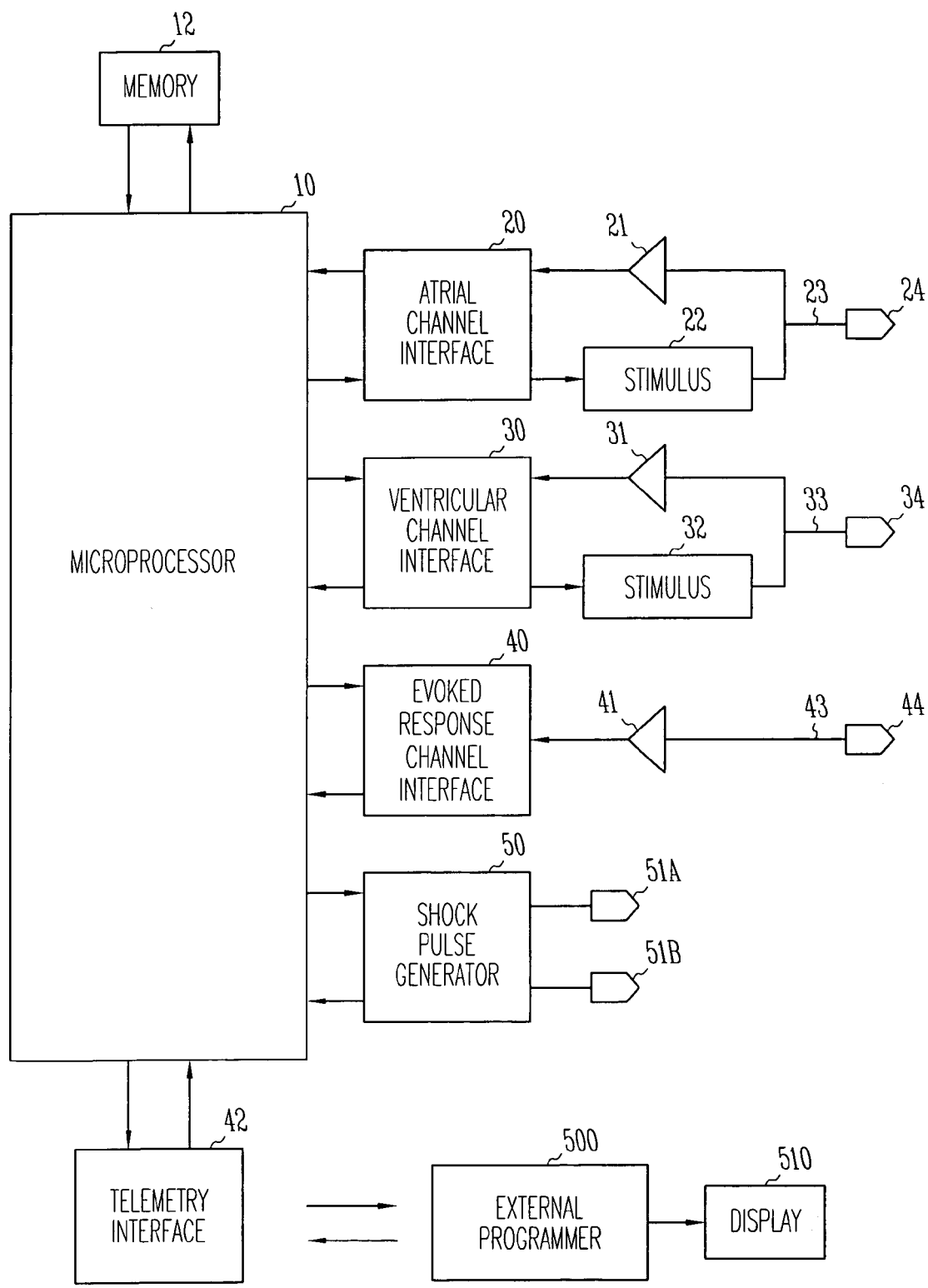
FIG. 1 is a block diagram of a cardiac rhythm management device with ATP and cardioversion/defibrillation capability.

FIG. 1 is a system diagram of a microprocessor-based cardiac rhythm management device with the capability of delivering cardioversion/defibrillation shocks as well as antitachycardia pacing therapy. The device may also be configured to deliver conventional (e.g., bradycardia) pacing as well. The controller 10 of the pacemaker is a microprocessor that communicates with a memory 12 via a bidirectional data bus. The memory 12 typically comprises a ROM (read-only memory) for program storage and a RAM (random-access memory) for data storage. The pacemaker has atrial and ventricular sensing/pacing channels that respectively include electrodes 24 and 34, leads 23 and 33, sensing amplifiers 21 and 31, pulse generators 22 and 32, and ventricular channel interfaces 20 and 30. A dedicated evoked response sensing channel is also provided that includes electrode 44, lead 43, sensing amplifier 41, and atrial channel interface 40. Incorporated into each sensing/pacing channel is thus a pacing channel made up of the pulse generator connected to the electrode and a sensing channel made up of the sense amplifier connected to the electrode. A switching network controlled by the microprocessor may be used to switch the electrodes from the input of a sense amplifier to the output of a pulse generator. In this embodiment, a single electrode is used for sensing and pacing in each channel, known as a unipolar lead. Other embodiments may employ bipolar leads that include two electrodes for outputting a pacing pulse and/or sensing intrinsic activity. The channel interfaces communicate bidirectionally with microprocessor 10 and include analog-to-digital converters for digitizing sensing signal inputs from the sensing amplifiers and registers that can be written to by the microprocessor in order to adjust the gain and threshold values for the sensing amplifiers. In the case of the atrial and ventricular channels, registers can be written to in order to output pacing pulses and change the pacing pulse amplitude and/or duration. A telemetry interface 40 is also provided for communicating with an external programmer 500 that has an associated display 510.

The controller 10 controls the overall operation of the device in accordance with programmed instructions stored in memory, including controlling the delivery of paces via the pacing channels, interpreting sense signals received from the sensing channels, and implementing timers for defining escape intervals and sensory refractory periods. The sensing circuitry of the pacemaker detects a chamber sense when a sense signal (i.e., a voltage sensed by an electrode representing cardiac electrical activity, sometimes called an electrogram signal) generated by a particular channel exceeds a specified intrinsic detection threshold. A chamber sense may be either an atrial sense or a ventricular sense depending on whether it occurs in the atrial or ventricular sensing channel. Pacing algorithms used in particular pacing modes employ such senses to trigger or inhibit pacing. Both bradycardia and anti-tachycardia pacing modes may be implemented in code executed by the controller.

2. Antitachycardia Pacing

The cardiac rhythm management device of FIG. 1 may be programmed with a plurality of selectable ATP pacing protocols that define the manner in which anti-tachycardia pacing is delivered. In a microprocessor-based device, the output of pacing pulses is controlled by a pacing routine that implements the selected pacing protocol as defined by various parameters. A data structure stored in memory contains the parameter sets that define each of the available pacing protocols. Pacing protocols for ATP therapy can generally be divided into two classes: those that deliver one or more pulses in timed relation to detected depolarizations and those that deliver a continuous pulse train for a specified time beginning after a detected depolarization. Both types of ATP protocols attempt to block the reentrant depolarization wavefront causing the tachycardia with a second depolarizing wavefront produced by a pacing pulse. Protocols of the first group may vary according to parameters that define the number of pulses delivered and the particular timing employed. Protocols of the second group include so-called burst pacing in which a short train of pulses is delivered for a specified time and may vary according to parameters that define the duration, frequency, and timing of the pulses.

The device delivers ATP therapy or a defibrillation shock under programmed control of the microprocessor in response to sensed activity from the sensing channels. A sensing routine analyzes the electrical activity received from the sensing channels in order to detect a tachyarrhythmia, and the tachyarrhythmia is then classified as a tachycardia (i.e., a terminable tachyarrhythmia) or fibrillation based upon rate and/or other criteria. The device detects a ventricular tachyarrhythmia, for example, by counting ventricular senses received via the ventricular sensing channel in order to measure the heart rate and determine whether the rate exceeds a selected threshold value. Once a tachyarrhythmia is detected, the rhythm is classified into either a tachycardia or a fibrillation zone by comparing the heart rate to a fibrillation rate boundary or by other means such as assessing the stability of the rhythm. If the tachyarrhythmia is classified as terminable, a pacing routine executed by the microprocessor delivers ATP pulses in accordance with the parameters of a selected protocol.

As noted above, the object of anti-tachycardia pacing is to create a pace-induced wavefront that propagates into the re-entrant circuit of the tachycardia and extinguishes it. Different protocols are apt to be more successful than others in terminating particular tachyarrhythmias that may differ as to rate and/or depolarization pattern. For this reason, modern cardiac rhythm management devices are capable of employing a number of different ATP protocols to deliver therapy. Pacing parameters affecting the magnitude and timing of the pulses can also be adjusted for each protocol. In order for a pacing pulse to have any effect, the pulse must capture the ventricle so that a propagating depolarization results. This is complicated by the fact that during a ventricular tachyarrhythmia, the action potential consumes a large portion of the total cycle length, leaving only a small window of time when the ventricle is non-refractory and even less time for an induced depolarization wavefront to propagate into the re-entrant circuit.

Ideally, a clinician would program the device to deliver pacing therapy using a protocol and parameters that will perform best for a particular patient's tachyarrhythmia. However, this may be difficult to predict, so that a conventional technique for dealing with this problem is to program the device to deliver a number of ATP pacing bursts using different protocols and/or adjustable pacing parameters. One such adjustable parameter is the coupling interval, which is the time from the last sensed depolarization to the first pacing pulse of a burst, commonly selected to be between 120 and 750 milliseconds. For capture to be achieved by that pacing pulse, the end of the coupling interval must occur when the ventricle is non-refractory. In a so-called scan mode, some devices vary the coupling interval of a series of bursts in a predetermined manner. When the ATP pacing burst consists of a train of pulses, the time between the pulses or cycle length is another parameter that can be adjusted as in a ramp-type burst where the cycle length increases or decreases with each pulse of the train.

3. Capture Verification

Conventional devices, however, do not obtain any information about how a particular ATP pulse or group of pulses affected the heart other than whether or not a tachyarrhythmia was terminated. It would be useful for the device to know if a particular ATP pulse was successful in capturing the heart since that information could be used to further adjust certain ATP parameters. According to the present invention, sensed electrical activity in a heart chamber resulting from a pace, referred to as an evoked response, is used to verify that capture was achieved. An evoked response sensing channel, which may be a dedicated channel or a sensing/pacing channel normally used to output pacing pulses and/or sense intrinsic activity, is used determine whether the pacing pulse has captured the heart chamber by detecting whether an evoked response occurs as a result of a pacing pulse. The particular channel used for evoked response detection should be one whose electrode is disposed in a location where an evoked response due to the pacing electrode can be most easily sensed. A ventricular sensing/pacing channel or a dedicated evoked response sensing channel with an electrode disposed in the paced ventricle, for example, could be used to detect evoked responses to ventricular paces.

In order to detect an evoked response, the sense signal generated by the evoked response sensing channel after a pacing pulse is compared with an evoked response detection threshold, which may be the same or different as the intrinsic detection threshold used to detect chamber senses. The evoked response detection threshold may also be adaptively adjusted as described in U.S. Pat. No. 6,192,275 issued to Zhu et al., and assigned to Cardiac Pacemakers, Inc., which is hereby incorporated by reference. The comparison between the sense signal and the evoked response detection threshold takes place within a defined period of time following output of the pacing pulse, referred to herein as a capture detection window. After a pacing pulse is output, an evoked response is either detected or not, signifying the presence or loss of capture, respectively.

Sensing channels are normally rendered refractory (i.e., insensitive) for a specified time period immediately following a pace in order to prevent the pacemaker from mistaking a pacing pulse or afterpotential for an intrinsic beat. To implement this function, the pacemaker controller ignores what would otherwise be detected chamber senses in the channel during the refractory interval. If the same sensing channel is used for both sensing intrinsic activity and evoked responses in a chamber, the capture detection window is then further defined as a period that supercedes the normal refractory period so that the pacemaker is sensitive to an evoked response even if no intrinsic events can be detected. For example, a ventricular sensing/pacing channel may be used to deliver ventricular paces, sense intrinsic ventricular beats, and detect evoked responses. During the capture detection window following a ventricular pace, the controller is prevented from detecting a ventricular sense but can still detect an evoked response if the sense signal exceeds the evoked response detection threshold.

It is also common practice to block the sensing amplifier of a sensing channel from receiving sense signals for a defined period of time that starts with a pacing pulse that is delivered through the same or a different channel, referred to as blanking. This is done in order to prevent saturation of the amplifier by the high voltage signal resulting from a pacing pulse. A separate period of time that overlaps the early part of a refractory interval is therefore defined, called a blanking interval, during which the sense amplifiers are effectively disabled. If a blanking interval is employed in an evoked response sensing channel, the blanking interval is followed by a capture detection window during which an evoked response may be detected by the evoked response sensing channel. In an exemplary embodiment, the blanking period may be approximately 10 ms, and the width of the capture detection window may range from 50 to 350 ms.

4. ATP with Capture Verification

Capture verification can be useful in delivering ATP therapy in a number of different ways. For example, capture verification can be used as feedback with the controller programmed to automatically adapt the coupling interval to assure that the first pulse of a burst captures the ventricle, thus eliminating the need to program a series of scanned bursts. The adaptation algorithm may operate so that the shortest possible coupling interval that still captures is found. Capture verification can also be used to assure that capture is maintained during a burst consisting of a pulse train. For example, in a ramp burst, the cycle length is progressively shortened from one pulse to the next, and capture verification can determine when the cycle length becomes too short and capture is lost. Once it is determined that the pulses are no longer capturing, the device can either terminate the burst or increase the cycle length. Capture verification can also be employed on a beat-to-beat basis to assure that capture is maintained at the fastest rate possible.

Capture verification can be used as part of a feedback system for automatically determining the best ATP protocol and/or parameter values to be used in a particular patient. For example, after selecting an ATP protocol and delivering a pacing burst, the controller counts and records the number of pacing pulses that failed to capture the ventricle. Future protocol selection can then be at least partially based upon which anti-tachycardia pacing protocol had the fewest number of recorded capture failures. The controller may also be programmed to automatically optimize the parameters of a given protocol based upon capture verification. For example, the controller may be programmed to use a particular ATP protocol with the cycle length and/or coupling interval initialized to preset values and to vary these parameters in accordance with the results of capture verification tests.

Figure 2A:
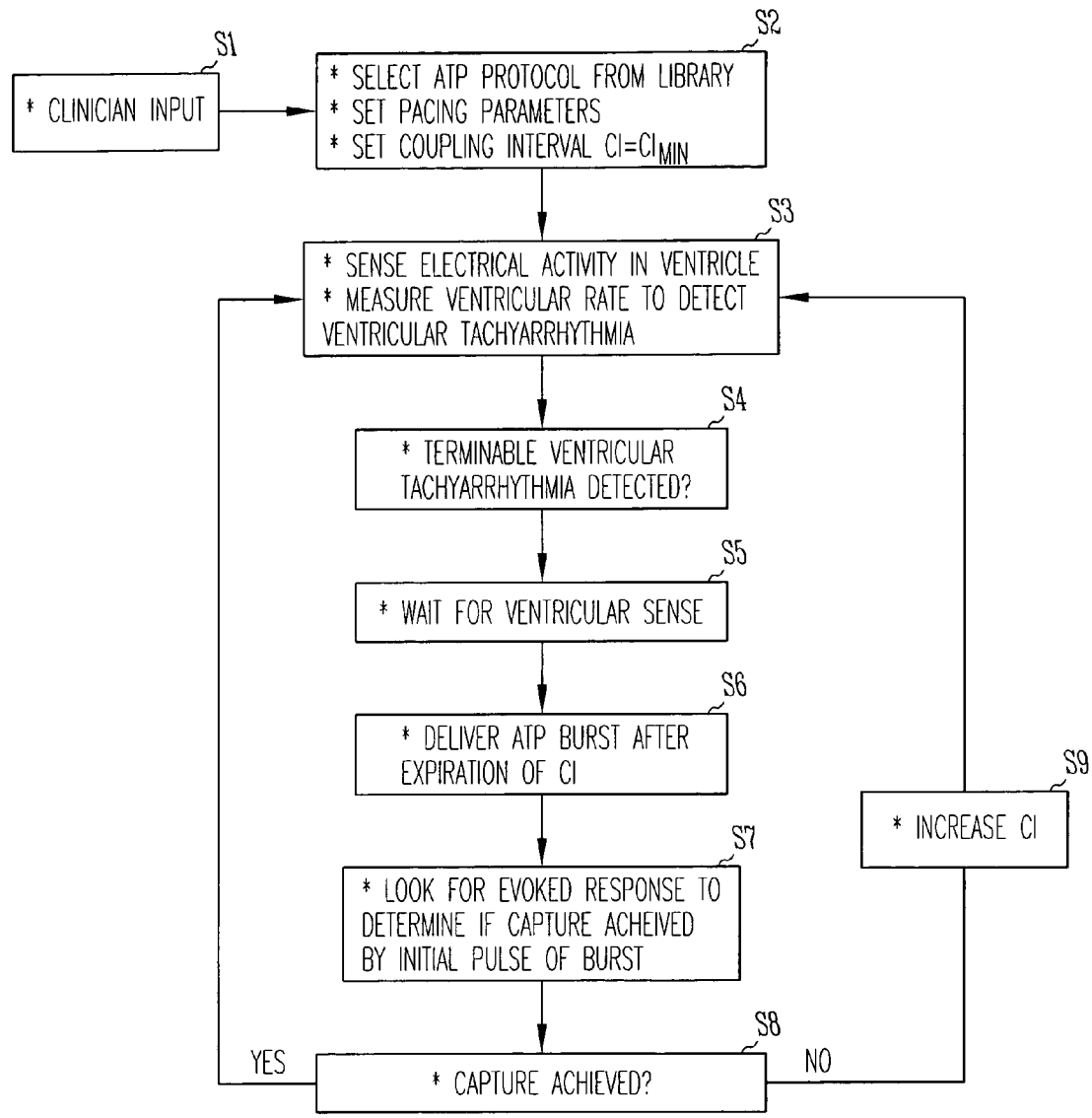
FIGS. 2A and 2B are flow diagrams showing the steps performed in a particular implementation.
Figure 2B:
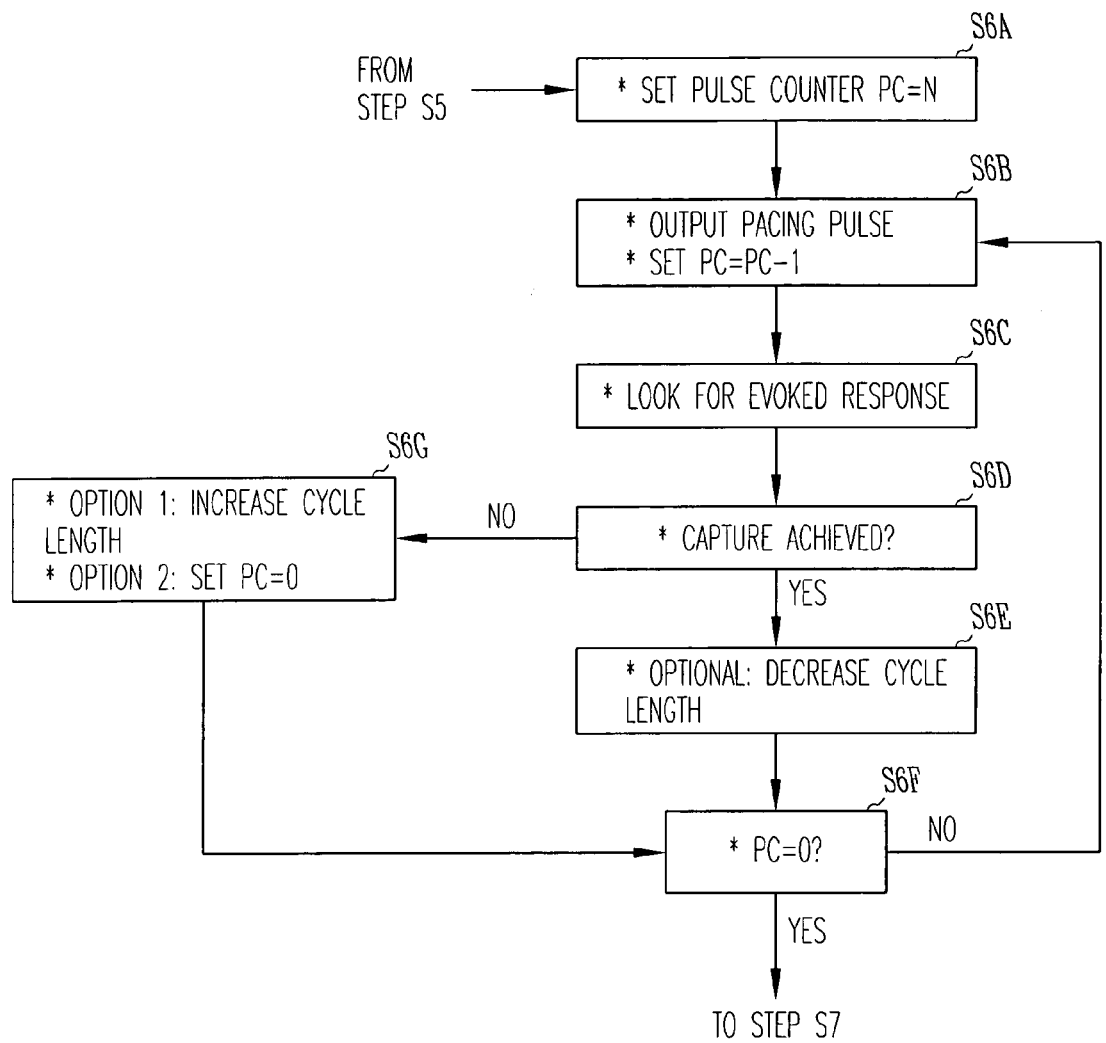

FIGS. 2A and 2B are flow diagrams showing the steps performed by a cardiac rhythm management device in one particular implementation of the invention. Referring first to FIG. 2A, the device is set up for delivering anti-tachycardia pacing therapy at step S2 where a particular ATP protocol is selected and various pacing parameter values are set, including the coupling interval CI. In this embodiment, the coupling interval is initially set to a specified minimum value $CI_{min}$. Clinician input for the set up procedure may be received via telemetry is received at step S1. At step S3, the device begins monitoring electrical activity in a ventricle via a sensing channel and counts ventricular senses to determine the ventricular rate. Using a rate-based criterion, the ventricular rate is classified as a terminable tachyarrhythmia when it falls within a specified zone. If a terminable tachyarrhythmia is detected at step S4, the device begins to deliver ATP therapy. The device then waits for the next ventricular sense at step S5 and starts a timer for the coupling interval CI. After expiration of the coupling interval, an ATP burst is delivered at step S6. As the term is used herein, a burst may consist of only one pacing pulse or a series of pacing pulses separated by a time interval referred to as the cycle length. In the latter case, the coupling interval is measured with respect to the initial pulse of the series. At step S7, the device looks for an evoked response after the initial (or sole) pulse of the burst through a ventricular sensing channel in order to determine if the pulse captured the ventricle. If capture is achieved as determined at step S8, the device returns to step S3. If the tachyarrhythmia has persisted, the process is then repeated. If the ATP burst did not achieve capture, the coupling interval CI is increased at step S9 before returning to step S3. By increasing the coupling interval, the burst is moved away from the refractory period caused by the preceding intrinsic depolarization. Once capture is achieved, the coupling interval is maintained constant for any subsequent bursts needed to terminate the tachyarrhythmia. In this implementation, the coupling interval is thus automatically set at the minimum interval needed to achieve capture.

FIG. 2B shows in more detail the steps performed at step S6 when the device delivers a series-type burst having multiple pacing pulses and capture is verified for each of pulse. At step S6a, a pulse counter PC is set to a value N representing the number of pulses in the series as defined by the protocol. At step S6b, the initial pacing pulse of the series is output after the coupling interval CI with respect to the previous intrinsic depolarization, and any subsequent pulses are output at a specified cycle length with respect to the previous pulse. The pulse counter PC is also decremented by one. After each pulse is output, an evoked response is looked for at step S6c. If capture is determined to have occurred at step S6d, the device then optionally decreases the cycle length if the selected ATP protocol is a ramp-type burst. If capture did not occur, the device optionally either increases the cycle length or sets the pulse counter PC to zero in order to terminate the burst. Next, the device tests the pulse counter at step S6f to see if the series of pulses has been completed. If not, the device returns to step S6b, and the steps are repeated. Otherwise, the device proceeds to step S7.

The above description has dealt with detecting ventricular tachycardias and delivering ATP therapy to the ventricles. Although not commonly employed at the present time, ATP therapy can be used to terminate atrial tachyarrhythmias. It should be appreciated that the invention may be used in conjunction with the delivery of ATP therapy to any heart chamber.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A method for delivery of anti-tachycardia pacing (ATP) therapy by a cardiac rhythm management device, comprising:
   generating sense signals representing electrical activity in a heart chamber and detecting a chamber sense when a sense signal exceeds a specified intrinsic detection threshold;
   delivering a burst of one or more pacing pulses in accordance with an anti-tachycardia pacing protocol;
   determining if one or more pacing pulses of the burst have captured the heart chamber; and,
   adjusting a timing parameter of the burst in accordance with the capture determination.

2. The method of claim 1 wherein the heart chamber is a ventricle.

3. The method of claim 1 wherein the burst is output after a specified coupling interval with respect to a chamber sense further comprising increasing the coupling interval when an initial pacing pulse of a burst has not captured the heart chamber.

4. The method of claim 1 where the burst is output after a specified coupling interval with respect to a chamber sense and further comprising:
   delivering a burst with the coupling interval set to a specified minimum value; and,
   increasing the coupling interval when an initial pacing pulse of a burst has not captured the heart chamber.

5. The method of claim 1 wherein the delivered burst is a train of pacing pulses separated by a specified cycle length and further comprising terminating the burst when a pacing pulse fails to capture the heart chamber.

6. The method of claim 5 wherein the burst is a ramp-type burst such that the cycle length between pacing pulses is progressively shortened with each pulse in the burst.

7. The method of claim 1 wherein the delivered burst is a train of pacing pulses separated by a specified cycle length and further comprising increasing the cycle length when a pacing pulse fails to capture the heart chamber.

8. The method of claim 1 further comprising selecting an anti-tachycardia pacing protocol and recording the number of pacing pulses that failed to capture the heart chamber when a burst in accordance with the protocol is delivered.

9. The method of claim 1 further comprising selecting an anti-tachycardia pacing protocol with the fewest number of recorded capture failures.

10. The method of claim 1 further comprising determining whether a pacing pulse has achieved capture by detecting whether an evoked response occurs during a capture detection window following the output of a pacing pulse.

11. A cardiac rhythm management device, comprising:
   a sensing channel for generating sense signals representing electrical activity in a heart chamber;
   a pacing channel for delivering paces to a selected heart chamber;
   a controller for controlling the delivery of pacing pulses in accordance with a programmed mode, detecting a chamber sense when the sense signal exceeds a specified intrinsic detection threshold, and detecting an evoked response when the sense signal following a pace exceeds a specified evoked response detection threshold; and,
   wherein the controller is further programmed to deliver a burst of one or more pacing pulses to the heart chamber in accordance with an anti-tachycardia pacing protocol upon detection of a tachycardia, determine whether a pacing pulse of the burst has captured the heart chamber, and adjust a timing parameter of the burst in accordance with the capture determination.

12. The device of claim 11 wherein the sensing and pacing channel are adapted to sense and pace a ventricle.

13. The device of claim 11 wherein the controller is programmed to deliver the burst after a specified coupling interval with respect to a chamber sense and to increase the coupling interval when an initial pacing pulse of a burst has not captured the heart chamber.

14. The device of claim 11 wherein the controller is programmed to deliver the burst after a specified coupling interval with respect to a chamber sense and further programmed to:
   deliver a burst with the coupling interval set to a specified minimum value; and,
   increase the coupling interval when an initial pacing pulse of a burst has not captured the heart chamber.

15. The device of claim 11 wherein the controller is programmed to deliver the burst as a train of pacing pulses separated by a specified cycle length and to terminate the burst when a pacing pulse fails to capture the heart chamber.

16. The device of claim 15 wherein the controller is programmed to deliver the burst as a ramp-type burst such that the cycle length between pacing pulses is progressively shortened with each pulse in the burst.

17. The device of claim 11 wherein the controller is programmed to deliver the burst as a train of pacing pulses separated by a specified cycle length and to increase the cycle length when a pacing pulse fails to capture the heart chamber.

18. The device of claim 11 wherein the controller is programmed to select an anti-tachycardia pacing protocol and record the number of pacing pulses that failed to capture the heart chamber when a burst in accordance with the protocol is delivered.

19. The device of claim 11 wherein the controller is programmed to select an anti-tachycardia pacing protocol with the fewest number of recorded capture failures.

20. The device of claim 11 wherein the controller is programmed to determine whether a pacing pulse has achieved capture by detecting whether an evoked response occurs during a capture detection window following the output of a pacing pulse.

* * * * *